(12) United States Patent
Matusch (10) Patent No.: US 9,302,048 B2
(45) Date of Patent: Apr. 5, 2016

(54) CYLINDER-PISTON UNIT WITH MULTI-PART PISTON

(71) Applicant: Rudolf Matusch, Marburg (DE)

(72) Inventor: Rudolf Matusch, Marburg (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 14/275,985

(22) Filed: May 13, 2014

(65) Prior Publication Data

US 2014/0249470 A1 Sep. 4, 2014

Related U.S. Application Data

(63) Continuation-in-part of application No. PCT/EP2012/072506, filed on Nov. 13, 2012.

(30) Foreign Application Priority Data

Nov. 16, 2011 (DE) .......................... 10 2011 119 204

(51) Int. Cl.
  *A61M 5/30* (2006.01)
  *A61M 5/24* (2006.01)
  *A61M 5/31* (2006.01)
  *A61M 5/315* (2006.01)
  *A61M 5/20* (2006.01)

(52) U.S. Cl.
  CPC . *A61M 5/30* (2013.01); *A61M 5/24* (2013.01); *A61M 5/3134* (2013.01); *A61M 5/31513* (2013.01); *A61M 2005/2013* (2013.01); *A61M 2005/2488* (2013.01); *A61M 2005/3118* (2013.01); *A61M 2005/31521* (2013.01); *A61M 2205/0222* (2013.01); *A61M 2205/19* (2013.01)

(58) Field of Classification Search
  CPC ................. A61M 2205/0222; A61M 2205/19; A61M 5/31513; A61M 5/31515; A61M 5/3134; A61M 2005/31521; A61M 2005/31523; A61M 2005/3112; A61M 2005/3123
  See application file for complete search history.

(56) References Cited

U.S. PATENT DOCUMENTS

| 789,092 | A | * | 5/1905 | Hulett ............... A61M 5/31513 604/222 |
| 1,521,890 | A | | 1/1925 | Klein |
| 2,756,748 | A | * | 7/1956 | Ferguson ...................... 604/222 |
| 6,142,977 | A | * | 11/2000 | Kolberg et al. ............... 604/218 |
| 6,213,977 | B1 | | 4/2001 | Hjertman |

(Continued)

FOREIGN PATENT DOCUMENTS

WO   WO 85/00524   2/1985

*Primary Examiner* — Nathan R Price
*Assistant Examiner* — Justin L Zamory
(74) *Attorney, Agent, or Firm* — R. S. Lombard; K. Bach (57) ABSTRACT

A cylinder-piston unit, of a needle-free injector, with at least one cylinder accommodating an injection solution, and with at least one piston. The piston is composed of a drive body and of a sealing body. The sealing body is at least one elastic disc, which bears under a radial clamping action against the inner wall of the cylinder. The drive body is a pot-shaped body with a peripheral elastic skirt. At least one area of the skirt bears under a radial clamping action against the inner wall of the cylinder. The cylinder chamber areas located in front of and behind the drive body communicate with each other via at least one recess. The drive body is arranged behind the sealing body in the cylinder, and the skirt faces towards the sealing body.

3 Claims, 4 Drawing Sheets

(56) References Cited

U.S. PATENT DOCUMENTS

| | | |
|---|---|---|
| 6,890,319 B1 | 5/2005 | Crocker |
| 2002/0013554 A1* | 1/2002 | Heinz ............... A61M 5/31511 604/222 |
| 2002/0193740 A1 | 12/2002 | Alchas et al. |
| 2003/0014006 A1 | 1/2003 | Alexandre et al. |
| 2007/0021716 A1 | 1/2007 | Hansen |
| 2008/0287885 A1 | 11/2008 | Hoffmann et al. |
| 2009/0099510 A1 | 4/2009 | Poulsen |
| 2009/0227942 A1 | 9/2009 | Hansen et al. |
| 2011/0166520 A1 | 7/2011 | Iwase et al. |
| 2011/0214777 A1 | 9/2011 | Matusch |
| 2011/0224612 A1* | 9/2011 | Lum ................. A61M 5/31511 604/125 |
| 2011/0270217 A1 | 11/2011 | Hansen et al. |

* cited by examiner

CYLINDER-PISTON UNIT WITH MULTI-PART PISTON

CROSS-REFERENCE TO RELATED APPLICATION

This is a continuation-in-part application of pending international application PCT/EP2012/072506 filed Nov. 13, 2012 and claiming the priority of German Application No. 10 2011 119 204.6 filed Nov. 16, 2011 which is hereby incorporated herein by reference in its entirety as though fully set forth

BACKGROUND OF THE INVENTION

The invention relates to a cylinder-piston unit of a needle-free injector, with at least one cylinder accommodating an injection solution, and with at least one piston.

DE 10 2005 054 600 discloses a cylinder-piston unit of a needle-free injector, of which the cylinder and the piston at least temporarily enclose an injection solution. At its front end, the cylinder has at least one outlet nozzle. In the front area, the piston has an elastic skirt, of which the front outer edge, when the piston is unloaded, covers a cross-sectional surface area larger than a cross-sectional surface area of the inner wall of the cylinder.

Pistons of this kind cannot generally be fitted free of bubbles into an already filled cylinder of a cylinder-piston unit. For this purpose, a so-called vacuum applicator machine is generally needed.

Another method by which a stopper is placed at ambient pressure onto the surface level of the already filled injection solution is one in which it is radially compressed by means of a multi-finger gripper and placed onto the liquid level. However, this can only be done with elastic pistons, e.g. made of a rubber mixture, which do not generally seal up to $350*10^5$ Pa and are therefore unsuitable for needle-free injectors.

U.S. Pat. No. 1,521,890 A describes a metallic syringe from medicine, having a piston which manages without a rubber-like sealing means. For this purpose, the piston has the shape of a forwardly open pot, in the bottom of which a central inner thread is arranged. By way of the inner thread, the piston is screwed onto the piston rod such that the latter also protrudes forwards from the pot. The pot wall bearing on the cylinder tapers towards the front. A frustoconical expansion body sits in the hollow space of the pot. It is likewise screwed onto the piston rod. When the expansion body is screwed in, the pot wall is pressed against the cylinder wall.

The object of the present invention is therefore to develop a piston whose components, at ambient pressure, can be set down at least partially on the liquid level of a filled cylinder in a bubble-free, sterile and gas-tight manner and which nevertheless withstands a high compression pressure without leakage during regular emptying of the cylinder-piston unit.

SUMMARY OF THE INVENTION

This object is achieved, according to the invention, by the features of claim 1. The piston is composed of a drive body and of a sealing body. The individual sealing body, which is set down on the liquid level of the injection solution, is at least one disc which is made from a rubber-like or a silicone-like material and which bears under a radial clamping action against the inner wall of the cylinder. The drive body is a pot-shaped body with a peripheral elastic skirt. At least one area of the skirt bears under a radial clamping action against the inner wall of the cylinder. The cylinder chamber areas located in front of and behind the drive body communicate with each other via at least one recess. The drive body is arranged behind the sealing body in the cylinder, and the skirt faces towards the sealing body. The drive body, which is forwardly displaceable upon actuation, can almost completely receive the sealing body during the forward travel, such that the combination of the drive body and of the sealing body has the function of a piston.

Here, the cylinder-piston unit of a needle-free injector, for example, is proposed by the invention. The injector, which can also be a disposable injector, not only accommodates the cylinder-piston unit but also a drive mechanism that is installed in an injector housing and that acts on a piston-actuating ram. As possible drive mechanisms, it is possible to use spring accumulators, gas drives with openable gas cartridges, or pyrotechnic drives. Known spring energy accumulators use pretensioned mechanical or pneumatic springs or spring systems. If a spring energy accumulator known from DE 10 2010 010 699 A1 is used as drive mechanism, the piston-actuating ram is held with a form fit, via at least one support rod or draw hook arranged on or in the injector housing, in order to pretension and hold this spring energy accumulator. The one or more support rods or draw hooks are retained in their locked position by means of one or more trigger elements until the use of the disposable injector. To trigger the injector, the one or more support rods or draw hooks are released, such that the piston-actuating ram, under the effect of the spring energy accumulator, can move at least approximately parallel to the centre line of the disposable injector, with the result that the injection solution present in the cylinder of the cylinder-piston unit is expelled via at least one nozzle.

The division of the piston into a drive body and a more elastic sealing body results in a structural separation of functions. On the one hand, there is the very elastic sealing piston which, as a disc, can be radially compressed by a multi-finger gripper in such a way that its external diameter for the fitting procedure is smaller by a few tenths of a millimeter than the internal diameter of the cylinder receiving it. After the multi-finger gripper has been pulled back, it sits gas-tight and bubble-free on the injection solution. The sealing body thus performs the function of simple gas-tight closure of the injection solution on the cylinder side opposite the regular cylinder outlet opening. The arrangement composed of the cylinder, the protective housing, the sealing stopper and the enclosed injection solution can be easily produced in a sterile manner.

On the other hand, there is the drive body that is to be used in a subsequent step. The drive body, made of a dimensionally stable and possibly self-lubricating plastic, is placed, with its skirt towards the front, behind the sealing body. Its elastic skirt bears sealingly, and in a manner secure against slipping, on the inner wall of the cylinder. When the injector is triggered, the drive body is suddenly moved by the piston-actuating ram against the sealing body sitting on the liquid level. The drive body thrust forwards carries the sealing body almost completely with it in its forward travel. The elastic sealing body presses the skirt, supported by the pressure of the liquid, sealingly against the inner wall of the cylinder according to the self-help principle. The drive body thus has the function of a regular piston. In the cylinder, it separates the low-pressure side from the high-pressure side sealingly and in a dimensionally stable manner. By contrast, the sealing body now only has the function of closing the air release bore present in the drive body.

BRIEF DESCRIPTION OF THE DRAWINGS

Further details of the invention will become clear from the dependent claims and from the following descriptions of schematically depicted illustrative embodiments.

DETAILED DESCRIPTION OF THE PARTICULAR EMBODIMENTS

Figure 1:
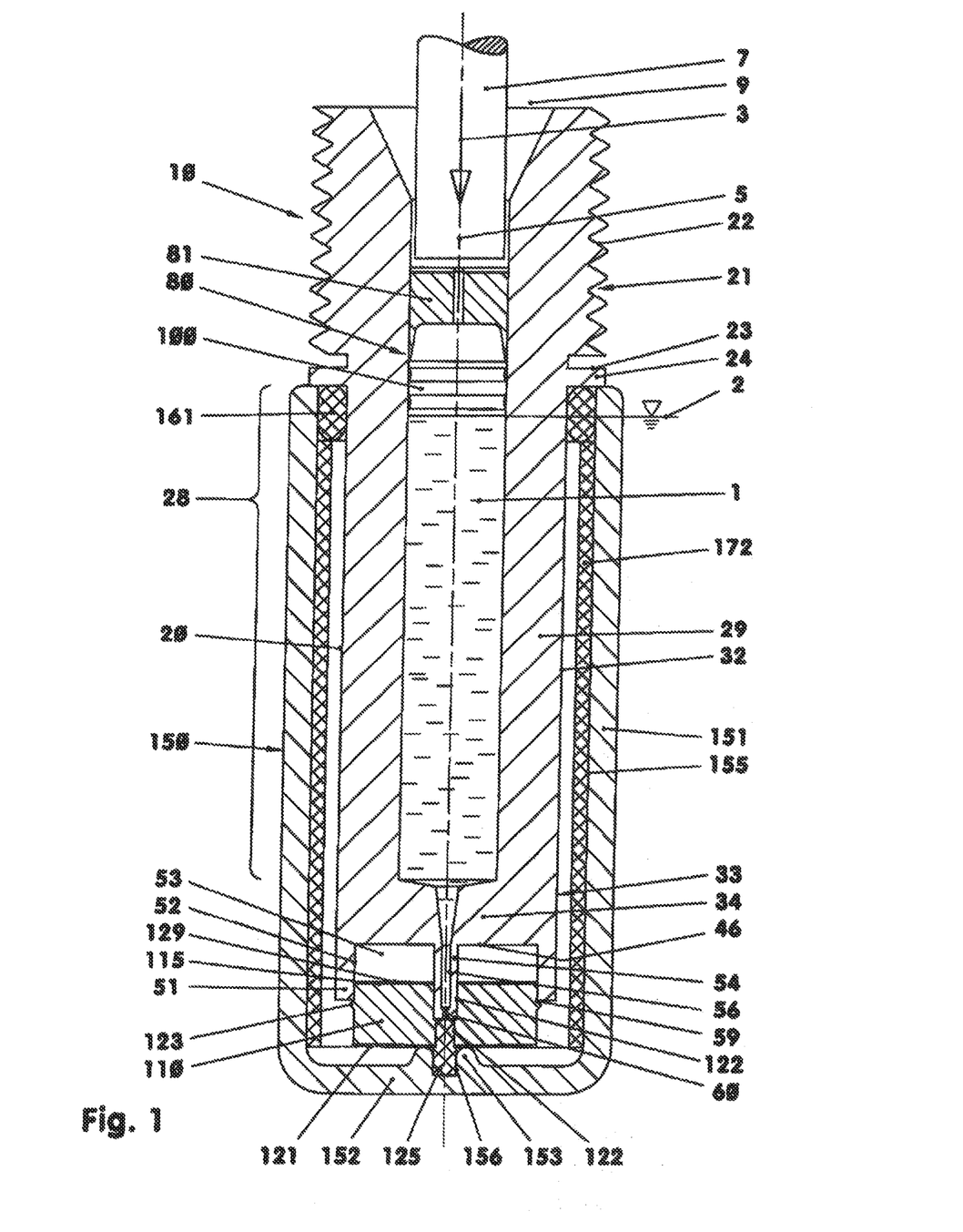
FIG. 1 shows a cylinder-piston unit with integrally formed discharge tube and protective housing.

FIG. 1 shows a cylinder-piston unit (10) of a needle-free injector. The cylinder-piston unit (10) is composed of a cylinder (20) and of a two-part piston (80). The cylinder (20) is additionally surrounded, for example, by a protective housing (150). Above the piston (80), the lower part of a piston-actuating ram (7) is shown, which belongs to the injector (not depicted here). The cylinder (20) is secured on the injector by means of its outer thread (22), present in the rear area of the cylinder, or by means of slits (23).

The for example one-part cylinder (20) is composed of a housing adapter (21), a tube portion (28) and a bottom portion (33). With the housing adapter (21), the cylinder (20) is fixed in an injector housing (not depicted). For this purpose, its radial outer wall has an outer thread (22) and/or at least two slits (23) lying opposite each other. The slits (23) have, for example, a depth that corresponds to the difference of thread outer diameter and thread root diameter. They are located at the thread end in immediate proximity to the tube portion (28). The width of the slits (23) corresponds, for example, to half their depth.

Between the slits (23) and the tube portion (28), there is an abutment web (24), of which the external diameter is identical to the outer diameter of the thread. The external diameter of the tube portion (28) is more than twice as great as the diameter of the inner wall (31). It is dimensioned such that its material withstands at least a pressure load of $350*10^5$ Pa (pascals).

The housing adapter (21) is adjoined by the cylinder wall (29) of the tube portion (28). Along the length of the tube portion, the cylinder wall (29) has, for example, a constant wall thickness of 3.25 mm.

The bottom portion (33) comprises an outwardly plane bottom plate (34), which corresponds to the mean wall thickness of the cylinder wall (29) in the area of the tube portion (28). An annular web (51), e.g. in the shape of a cylindrical tube, is integrally formed in the outer area of the bottom plate (34). The annular web (51), which encloses a receiving space (53) for the adhesive disc, is, for example, as high as the wall thickness of the bottom plate (34). The wall thickness of the annular web (51) is about one third of the wall thickness of the cylinder wall (29) of the tube portion (28).

The discharge tube (54) supporting the outlet nozzle (60) is arranged in the centre of the plane bottom plate (34). The discharge tube (54), of which the external diameter measures 2.25 mm for example, has a front end which protrudes about one millimeter beyond the annular web (51). Lying between the at least approximately cylindrical outer wall of the discharge tube (54) and the cylindrical inner wall (52) of the annular web (51), there is a receiving space (53), e.g. with a depth of 3 mm, for the adhesive disc.

The end face (58) of the discharge tube (54) (cf. FIG. 2) is spherically curved, at least in part, or plane. The outlet nozzle (60) lying to the front has an internal diameter of 0.2 to 0.4 mm, whereas the internal diameter of the bore (56) leading to the outlet nozzle (60) measures about 0.5 to 1 mm, at least in its front half.

Figure 2:
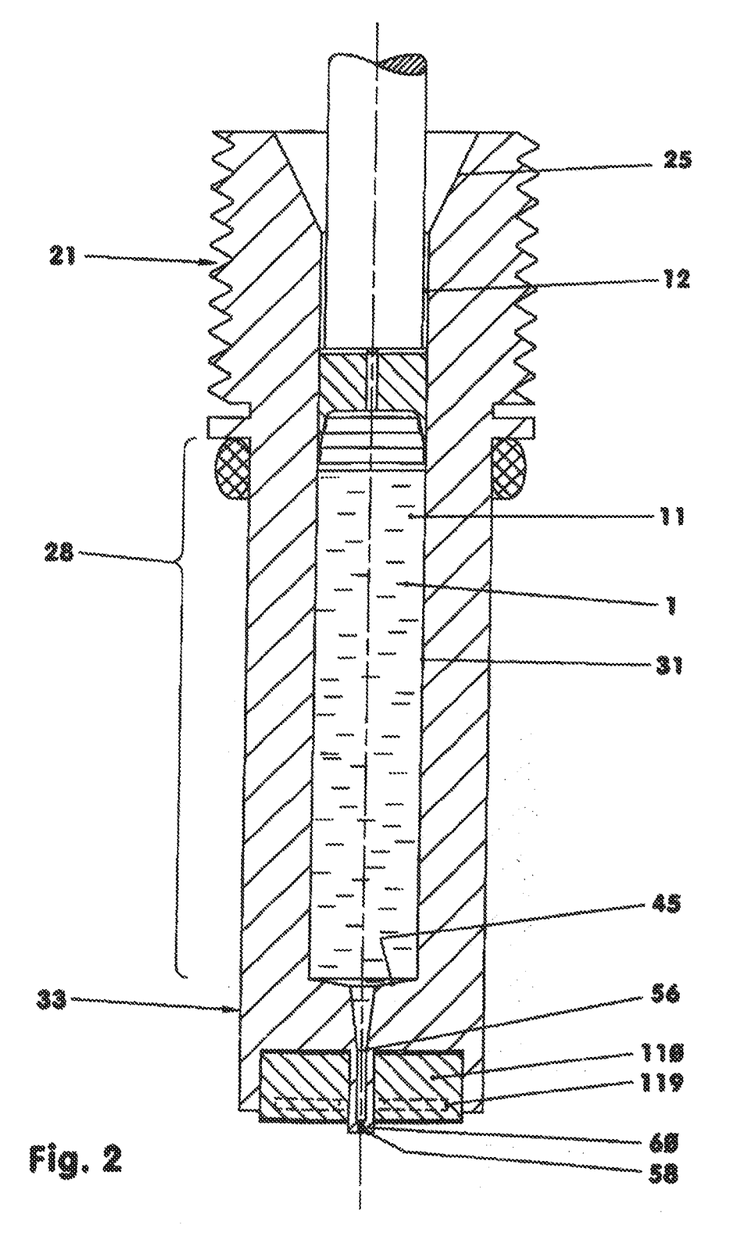
FIG. 2 shows the same as FIG. 1, but without the protective housing (injector already sits on the skin of the patient)

According to FIG. 2, the inner wall (31) of the cylinder is shaped at least approximately cylindrically, at least in the tube portion (28). It there has an internal diameter of 5.5 mm, for example. In the area of the housing adapter (21), the inner wall (31) of the cylinder widens out in the shape of a truncated cone. The cone angle of this widening (25) is 50 degrees, for example. The length of the widening (25) corresponds to about one third of the length of the housing adapter (21).

In the area of the bottom portion (33), the inner wall (31) of the cylinder ends in a cylinder bottom (45), of which the cone angle measures 160 degrees, for example. A discharge bore (56) is located between the cylinder bottom (45) and the outlet nozzle (60) arranged in the discharge tube (54), said discharge bore (56) having a cylindrical wall at least in the area before the outlet nozzle (60). In the illustrative embodiment, the rear portion of the bore (56) directed towards the cylinder bottom (45) is designed as a truncated cone. It has a cone angle of 12 degrees, for example. It extends, for example, in the area of the wall of the bottom plate (34).

According to FIG. 1, an adhesive disc (110) is arranged between the discharge tube (54) and the annular web (51), in the front area of the receiving space (53) for an adhesive disc. It has a material thickness that is at least 0.4 mm greater than the depth of the receiving space (53) for the adhesive disc. The adhesive disc (110) has a central bore (122), of which the internal diameter is, for example, 0.5-1 mm smaller than the external diameter of the discharge tube (54). Thus, the front area of the discharge tube (54) is surrounded tightly and closely by the rear area of the bore (122). The front and still unexpanded area of the bore (122) thus appears with a smaller diameter in FIG. 1.

The substantially cylindrical outer wall of the adhesive disc (110) is guided on the cylindrical inner wall (52) of the annular web (51). According to FIG. 1, the adhesive disc (110) has, in the upper area of its outer wall, a circumferential web (123) which protrudes radially, e.g. by 0.5 mm, and via which the adhesive disc bears elastically on the front inside edge (59) of the annular web (51).

For positioning the adhesive disc (110) on the annular web (51) of the bottom portion (33), the latter can also have a radially inwardly protruding web, which is integrally formed in the front area of the annular web (51) and which protrudes elastically into a corresponding annular groove of the adhesive disc (110).

The adhesive disc (110) is made of rubber, for example, or of another elastomer and is provided, on its two plane front end faces, with an adhesive layer (121, 129) composed, for example, of a pressure-sensitive adhesive. The rest of the surface areas have good sliding ability, since the adhesive disc (110) is at least partially treated with silicone oil or coated with Teflon.

A stiffening disc (119) can be inserted into the adhesive disc (110). It is shown in FIG. 2 by broken lines. This stiffening disc (119), e.g. encapsulated or vulcanized in, has a wall thickness of 0.5-1 mm, for example. It is made from a conventional ferrous or non-ferrous metal, for example. Its bore is at least 1 mm larger than the external diameter of the discharge tube (54). The external diameter of the stiffening disc (119) is, for example, 1-2 mm smaller than the external diameter of the adhesive disc (110). The stiffening disc (119), here integrated into the adhesive disc (110), is positioned for example 0.5 to 1 mm behind the front adhesive layer (121). The centre lines of the adhesive disc (110) and of the stiffening disc (119) are congruent.

If appropriate, the adhesive disc (110) has at least one lateral notch, which is oriented parallel to the centre line (5) and by means of which, upon insertion of the adhesive disc (110) into the receiving space (53), the air present therein can be easily displaced. The air can also escape via a bore arranged in the annular web (51), in proximity to the end face (46) of the bottom portion (33).

The pot-shaped protective housing (150), a sterile closure, which is made of glass for example, is composed here of a tubular jacket (150) and of a plane bottom (152). The cylindrical, smooth outer wall (32) of the tube portion (28) and of the bottom portion (33), with the inserted adhesive disc (110), of the cylinder (20) is here surrounded by the protective housing (150). In the area of the tube portion (28), the distance between the outer wall (32) of the tube portion (28) and the inner wall (155) of the protective housing (150) is 1.5 mm, for example. The axial distance between the bottom (152) of the protective housing (150) and the adhesive disc (110) measures 1 mm, for example, according to FIG. 1.

The protective housing (150) is fixed releasably on the cylinder (20) at two locations. The first location lies at the transition between the tube portion (28) and the abutment web (24) of the cylinder (20). There, according to FIG. 1, an O-ring (161) seals the protective housing (150) in relation to the cylinder (20). At the same time, the O-ring centres the protective housing (150) on the cylinder (20). Instead of a conventional O-ring (161), it is also possible to use a quad ring, a profiled ring or the like.

Upon assembly, the sealing ring (161) is clamped between the protective housing (150) and the cylinder (20), such that, in addition to the sealing function, it can also easily perform a centring and holding function. If appropriate, the sealing ring (161) can also be replaced by a tough sealing adhesive.

The second location for supporting the protective housing (150) on the cylinder (20) is situated centrally in the bottom (152) of the protective housing (150). A central blind bore (156) is arranged there and is surrounded by an inwardly protruding supporting web (153) formed integrally on the bottom (152). The annular supporting web (153) bears, with its for example half-toric end face, on the adhesive disc (110).

A stepped rubber stopper (125) sits in the blind bore (156), either clamped or adhesively bonded therein. The rubber stopper (125) lies sealingly with its rear end in front of the outlet nozzle (60) of the discharge tube (54). Its front end engaged in the blind bore (156) has a diameter which, for example, is 0.5 mm greater than that of its rear end. The rubber stopper (125) fixes the front end of the protective housing (150) radially over the adhesive disc (110), which bears on the annular web (51) of the cylinder (20).

A rectangular piece of cotton woven fabric (172), for example, is placed as moisture-retaining material (171) in the protective housing (150). The cotton woven fabric (172) bears partially or completely on the inner wall (155) of the protective housing (150). Before being put in place, it is moistened to saturation with, for example, distilled or sterile water. Suitable active substances can also be added to the water to counter microbial contamination.

According to FIG. 1, the cylinder (20) is partially filled with an injection solution (1). The liquid level (2) of the injection solution (1) is situated in the transition area between the housing adapter (21) and the tube portion (28). A disc-shaped sealing body (100) is placed on the liquid level (2) in a sterile manner and without bubbles and, under the effect of radial clamping, bears sealingly on the inner wall (31) of the cylinder. A pot-shaped drive body (81) is arranged behind the sealing body (100). The drive body (81) bears partially on the sealing body (100) or is at a distance of, for example, 0.2 to 0.5 mm therefrom.

Figure 4:
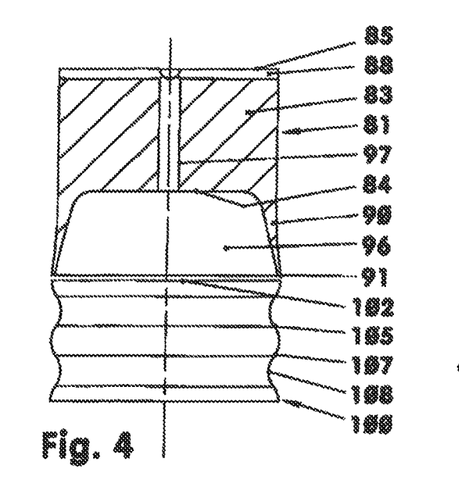
FIG. 4 shows drive body and sealing body outside the cylinder.

The sealing body (100) here is a disc whose undeformed diameter is, for example, twice as great as its disc thickness (cf. FIG. 4). On its circumference, this disc (100) has, for example, a grooved profile (107) with, for example, two grooves (108). The grooved profile (107) is, for example, configured such that the sealing body (100) has, in cross section, a wave line with two wave valleys forming the grooves (108). The wave line is composed here of arcs of a circle.

The circumference of the disc (100) can alternatively have a grooved profile for the endless flutes and grooves of which the flute cross sections are known, for example, from trapezoidal threads, flat threads and buttress threads. In the flute cross sections of the buttress threads, the normals of the two flanks of a flute should enclose angles of up to 180 degrees.

If appropriate, the radial outer wall of the disc (100) can also have a smooth cylindrical surface.

Figure 3:
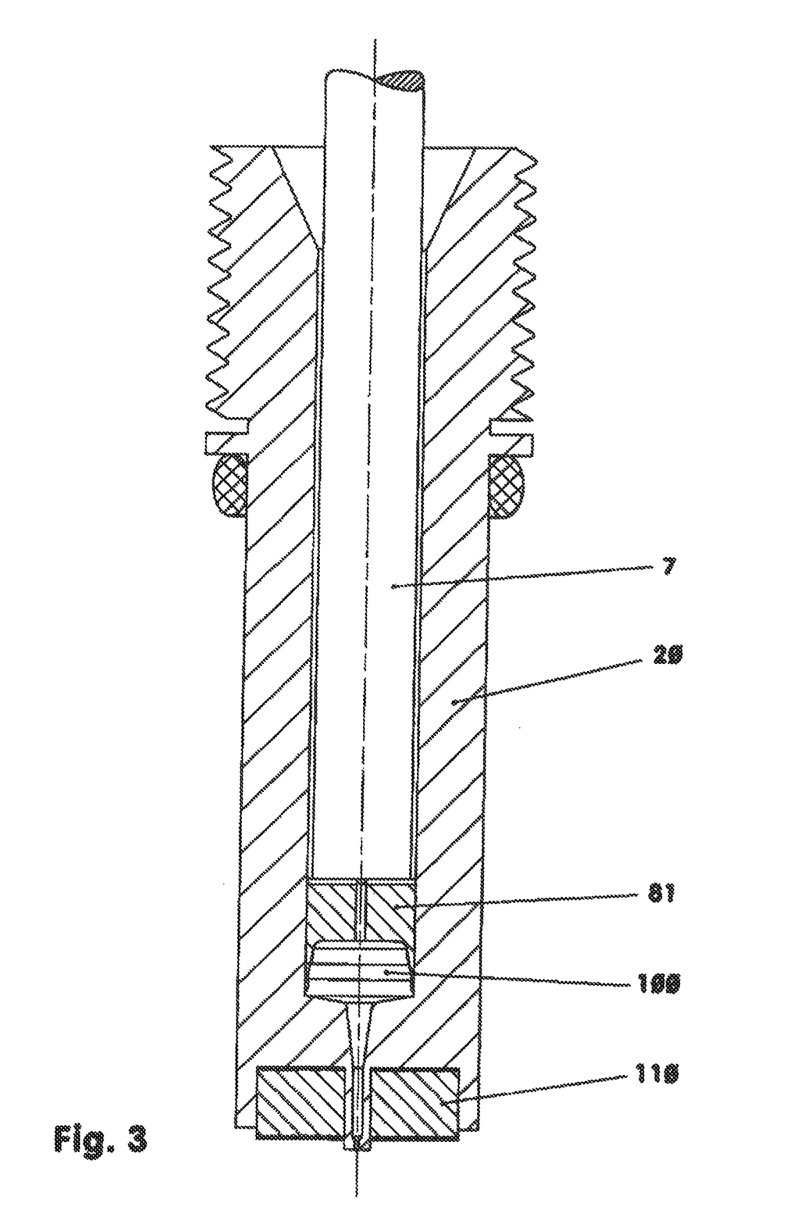
FIG. 3 shows the same as FIG. 2, but after the injection solution has been expelled (injector still sits on the skin of the patient)
Figure 5:
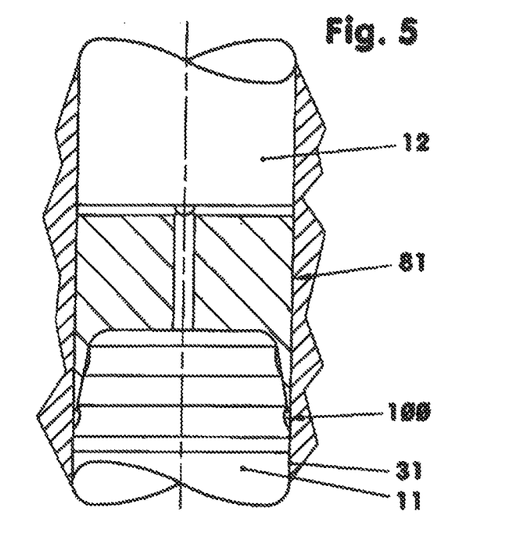
FIG. 5 shows drive body and sealing body from FIG. 4 in the cylinder after assembly.

Since the sealing body (100) is an elastic component, e.g., made from an elastomer, the wave crests of the fitted sealing disc are flattened off (cf. FIGS. 2, 3 and 5).

The pot-shaped drive body (81), whose length corresponds to its external diameter for example, is composed of a disc-shaped impact plate (83) and of a skirt (90) formed integrally thereon. The thickness of the impact plate (83) is here slightly greater than the length of the skirt (90) (cf. FIGS. 4 and 5). It can be produced from, inter alia, polytetrafluoroethylene (PTFE), perfluoroalkoxy polymer (PFA), from the fluoroelastomer perfluoroethylene propylene copolymer (FEP) or from ethylene tetrafluoroethylene (ETFE), wherein the first-mentioned material has the lowest coefficient of friction.

The impact plate (83), which is impacted by the piston-actuating ram (7) when the injector is triggered, has at least a for example central bore (97), by which the cylinder chamber areas (11, 12) located in front of and behind the drive body (81) are connected to each other with minimal restriction. The bore (97), which can also extend obliquely with respect to the centre line (5), has a minimum diameter of between 1 and 2 mm. According to the illustrative embodiments, the bore (97) ends on the rear face (85) of the drive body (81), e.g. in a channel intersection (88) composed of two channels intersecting in the area of the bore (97). The channels of the channel intersection (88) each have a semicircular cross section, wherein the diameter of the cross sections corresponds, for example, to the diameter of the bore. Of course, the channels of the channel intersection (88) can also have triangular cross sections or any other desired cross sections.

The front face (84) of the impact plate (83) is adjoined by the skirt (90), which is designed as an elastic sealing lip. Starting from the front face (84), the wall of the skirt (90) tapers towards the front outer sealing edge (91), which bears elastically on the inner wall (31) of the cylinder in each operating state of the injector. In the installed state, the skirt (90) and the front face (84) enclose an immersion space (96). The latter has substantially the shape of a truncated cone, of which the cone angle measures 20 degrees, for example.

Of course, the immersion space (96) enclosed by the impact plate (83) and the skirt (90) includes all shapes of depressions into which a sealing body (100) can engage. The immersion space (96) can thus have an n-gonal to polygonal cross section. In addition to the described trapezoidal surface, at least one longitudinal section can have a rectangular surface, a triangular surface, the surface of a semicircle, of a segment of a circle, of a sector of a circle, or such like.

Figure 6:
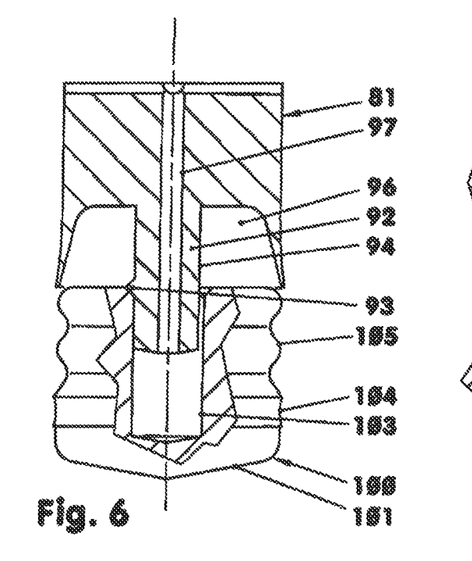
FIG. 6 shows the same as FIG. 4, but the drive body has a stub.
Figure 7:
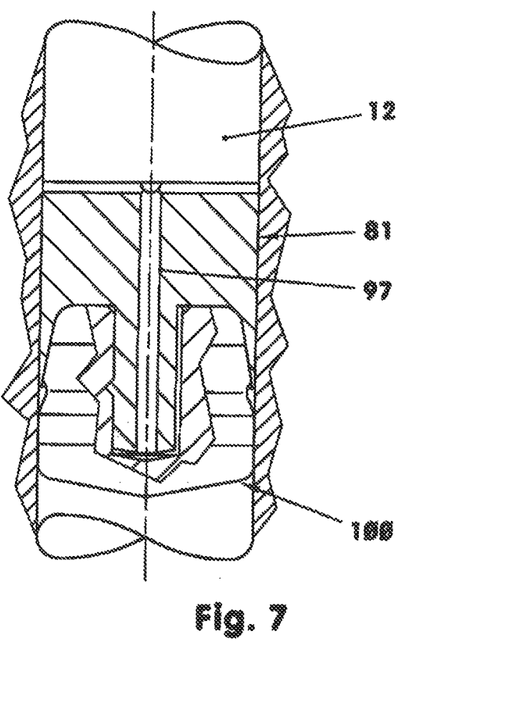
FIG. 7 shows drive body and sealing body from FIG. 6 in the cylinder after assembly upon actuation.

FIGS. 6 and 7 show a piston (80) as a combination of the drive body (81) and of the sealing body (100), in which the drive body (81) is centred in the blind bore (103) of a stopper-shaped sealing body (100) via a stub (92). As in a larger disposable syringe, the sealing body (100) here has an explicitly formed sealing web (104), which is arranged a few tenths of a millimeter behind a conical front end face (101). To the rear, the sealing web (104) is adjoined by a corrugated profile, as is known at least approximately from FIG. 4. The central blind bore (103) of this elastic sealing body (100) has a 45° bevel of 0.5 mm in width.

According to FIG. 6, the stub (92) of the drive body (81) has, on its right-hand side, a flattening (94) which extends across its entire length. Moreover, in some areas, it has an abutment web (93) via which the drive body (81), with the injector not yet triggered, bears on the 45° bevel of the blind bore (103) of the sealing body (100).

The blind bore (103) has a depth which is at least approximately as long as the length of the stub (92). It will be seen from FIG. 7 that, when the sealing body (100) enters the immersion space (96), the air to be displaced from the immersion space (96) flows along the flattening (94) into the bore (97), in order to pass from there into the rear cylinder chamber area (12).

The combination (80) of the drive body (81) and of the sealing body (100) permits simple bubble-free, sterile filling, and a closure of the cylinder-piston unit (10) in connection with an ejection procedure upon release of the injector, which withstands a very high compression pulse of up to $350*10^5$ Pa.

For the bubble-free closure of the cylinder (20) filled with the injection solution (1), the sealing disc is held, e.g. at ambient pressure, with the aid of a three-finger gripper on its outer wall (105) and, by means of the fingers of the three-finger gripper, is compressed radially until the fingers of the three-finger gripper can place the sealing disc (100) without difficulty onto the liquid level (2) in the cylinder (20). The fingers of the three-finger gripper spreading out in the cylinder (20) are pulled back, while the rear face (102) of the sealing disc (100) is held in its position by means of a retainer.

Of course, this procedure can also be carried out in a vacuum machine.

After the sealing disc (100) has been fitted, the drive body (81) is placed, with the skirt (90) towards the front, into the cylinder (20) behind the sealing disc (100). The drive body (81) stays in this rear position on account of the radial clamping force of the skirt (90) designed as an elastic sealing lip. As can be seen in FIGS. 4 and 6, the elastic skirt (90) protrudes outwards beyond the outer contour of the impact plate (83) when the drive body (81) is located outside the cylinder (20).

When the injector is ready for the injection, the protective housing (150), together with the cotton woven fabric (172), is pulled off from the front of the cylinder (20), e.g. by manual force. The rubber stopper (125) remains hanging on the protective housing (150), while the sealing ring (161) remains on the outer wall (32) of the cylinder (20).

To be able to administer the injection solution, the injector, with the adhesive disc (110) towards the front, is placed onto the skin surface of the patient. By the pressing force of the injector, the adhesive disc (100) is loaded in such a way that, with the locking action of the circumferential web (123) being overcome, it slips along the discharge tube (54) in the direction of the bottom portion (33), such that the adhesive layer (129) of the rear face (115) affixes itself to the end face (46) of the bottom portion (33). The adhesive disc (110) now completely fills the receiving space (53) for the adhesive disc. In this procedure, the front adhesive layer (121) of the adhesive disc (110) affixes to the skin of the patient, and the discharge tube (54) protrudes a few tenths of a millimeter out of the adhesive disc (110).

The end face (58) of the discharge tube (54) forces an indent into the skin, in order to additionally tension the latter at the application site. At the same time, the injector is triggered by being pressed onto the skin. The piston-actuating ram (7), pretensioned by means of a mechanical or pneumatic spring, applies a sudden load to the piston (80), such that the injection solution (1) penetrates in a high-velocity jet through the tensioned skin of the patient.

The piston-actuating ram (7) first strikes with great force against the drive body (81), see arrow direction (3). The drive body (81) is pressed against the almost incompressible sealing disc (100) resting on the liquid level (2). The skirt (90) slides along the inner wall (31) of the cylinder via the outer wall (105) of the sealing disc (100). The sealing disc (100) enters the immersion space (96) of the drive body (81), cf. FIG. 5 or 7. The displaced air flows through the bore 97 and along the channel intersection (88) on the piston-actuating ram (7) into the external environment (9) of the injector.

The sealing disc (100) and the drive body (81) now form a virtually rigid combination, namely the piston (80), which pushes the injection solution (1) forwards. The sealing with respect to the inner wall (31) of the cylinder is taken over by the sealing edge (91) of the skirt (90), which is pressed on more strongly by the sealing disc (100) loaded by the pressure of the liquid. Since the coefficient of sliding friction of the sealing edge (91) is less than the coefficient of sliding friction of the sealing disc (100) because of the material used for the drive body, there is a low sliding-friction resistance despite the high sealing action.

LIST OF REFERENCE SIGNS

1 Injection solution
2 Liquid level
3 Arrow direction upon injector release
5 Centre line
7 Piston-actuating ram
9 Environment
10 Cylinder-piston unit
11 Cylinder chamber area in front of (81)
12 Cylinder chamber area behind (81)
20 Cylinder
21 Housing adapter
22 Outer thread
23 Slits
24 Abutment web
25 Widening on the inside
28 Tube portion
29 Cylinder wall
31 Inner wall of cylinder, inner wall, radial
32 Outer wall, radial
33 Bottom portion
34 Bottom plate
45 Cylinder bottom, inner side of the cylinder bottom
46 End face of the bottom portion, front
51 Annular web
52 Inner wall, cylindrical
53 Receiving space for adhesive disc
54 Discharge tube, plastic
56 Bore, inner bore
58 Face, end face
59 Front edge 60 Nozzle, outlet nozzle
80 Piston, combination of (81) and (100)
81 Drive body; body, pot-shaped
83 Impact plate
84 Front face
85 Rear face
88 Channel intersection
90 Elastic skirt; sealing lip
91 Edge, sealing edge
92 Stub
93 Abutment web
94 Flattening, notch
96 Immersion space, hollow space
97 Recess, bore, central
100 Sealing body, sealing disc
101 Front face
102 Rear face
103 Blind bore
104 Sealing web
105 Outer wall, profiled
107 Grooved profile
108 Groove
110 Adhesive disc, elastomer disc
115 Rear face
119 Stiffening disc
121 Adhesive layer, front, pressure-sensitive adhesive, adhesive coating
122 Bore, stepped
123 Circumferential web
125 Rubber stopper
129 Adhesive layer, rear, pressure-sensitive adhesive, adhesive coating
150 Protective housing, glass; outer shell; sterile closure
151 Jacket, tubular
152 Bottom, plane
153 Supporting web
155 Inner wall
156 Blind bore
161 O-ring
171 Moisture-retaining material
172 Woven fabric, cotton woven fabric

What is claimed is:

1. Cylinder-piston unit (10) of a needle-free injector, comprising:
   a cylinder (20) for accommodating an injection solution, and at least one piston (80),
   each of the at least one piston (80) includes a drive body (81) and a sealing body (100), the drive body (81) and the sealing body (100) in movable relationship with respect to one another during actuation of the cylinder-piston unit (10),
   the sealing body (100) for setting down on a liquid level (2) of the injection solution and includes at least one disc comprising an elastic material for bearing under a radial clamping action against an inner wall (31) of the cylinder (20),
   the drive body (81) includes a disc-shaped impact plate (83) proximate a rear face (85) thereof and having a peripheral elastic tapered sealing lip (90) proximate a front face (84) thereof, the peripheral elastic tapered sealing lip (90) has a front outer sealing edge (91) for bearing elastically with a radial clamping action against the inner wall (31) of the cylinder (20) in an operative position, an immersion space (96) is bordered by the front face (84) and the peripheral elastic tapered sealing lip (90) of the drive body (81), the immersion space (96) for receiving the sealing body (100) upon actuation of the cylinder-piston unit (10),
   the cylinder (20) having cylinder chamber areas located in front of and behind the drive body (81) in fluid communication with each other via at least one recess (97) of the drive body (81), either directly or by way of a valve,
   the drive body (81) is arranged behind the sealing body (100) in the cylinder (20), and the peripheral elastic tapered sealing lip (90) faces front towards the sealing body (100),
   the drive body (81), for being forwardly displaceable towards the sealing body (100) upon actuation, for about completely receiving the sealing body (100) in the immersion space (96) during the forward travel of the drive body (81), for causing the combination of the drive body (81) and of the sealing body (100) to function as the piston (80),
   each of the at least one recess (97) is a cylindrical bore of the drive body (81), in which the cylindrical bore is oriented parallel to a centre line (5) of the drive body (81),
   drive body (81) further includes a stub (92) in operative arrangement with the immersion space (96), and,
   the drive body (81) includes one of said at least one recess (97) oriented parallel to the center line (5) of the drive body (81) wherein the one of said at least one recess (97) passes through the stub (92).

2. Cylinder-piston unit according to claim 1, wherein the sealing body (100) has a central blind bore (103) in operative arrangement with the stub (92) for completely receiving and housing the stub (92) upon actuation of the cylinder-piston unit (10).

3. Cylinder-piston unit according to claim 2, wherein the stub (92) has an abutment web (93) in a predetermined position extending radially for bearing on the sealing body (100) proximate the central blind bore (103) prior to actuation of the cylinder-piston unit (10).

* * * * *